(12) United States Patent
Kato et al.

(10) Patent No.: US 8,951,773 B2
(45) Date of Patent: Feb. 10, 2015

(54) PRODUCTION METHOD FOR BIOFUEL

(75) Inventors: Hiroaki Kato, Nagareyama (JP); Ko Yamashita, Kawaguchi (JP); Yukio Fukushima, Matsudo (JP); Ken Amano, Hitachiota (JP); Takashi Kaneko, Tokyo (JP); Iwao Ueda, Tokyo (JP); Nobuo Aoki, Tokyo (JP); Kengo Suzuki, Tokyo (JP); Ryo Arashida, Tokyo (JP); Ryohei Nakano, Tokyo (JP)

(73) Assignees: Hitachi, Ltd., Tokyo (JP); JX Nippon Oil & Energy Corporation, Tokyo (JP); euglena Co., Ltd., Tokyo (JP)

( * ) Notice: Subject to any disclaimer, the term of this patent is extended or adjusted under 35 U.S.C. 154(b) by 0 days.

(21) Appl. No.: 13/699,780

(22) PCT Filed: May 25, 2011

(86) PCT No.: PCT/JP2011/061998
§ 371 (c)(1),
(2), (4) Date: Nov. 26, 2012

(87) PCT Pub. No.: WO2011/148981
PCT Pub. Date: Dec. 1, 2011

(65) Prior Publication Data
US 2013/0071889 A1 Mar. 21, 2013

(30) Foreign Application Priority Data
May 26, 2010 (JP) ................. 2010-121042

(51) Int. Cl.
*C12N 1/00* (2006.01)
*C12N 1/12* (2006.01)
(Continued)

(52) U.S. Cl.
CPC ............... *C12P 7/64* (2013.01); *C12P 7/6463* (2013.01); *C12P 7/649* (2013.01); *C10L 1/02* (2013.01); *C10G 2300/4043* (2013.01); *Y02E 50/13* (2013.01); *C10G 2300/1014* (2013.01)
USPC .................. 435/243; 435/257.4; 435/257.1

(58) Field of Classification Search
USPC .................. 435/243, 257.4, 252.1, 257.1
See application file for complete search history.

(56) References Cited

U.S. PATENT DOCUMENTS

2008/0160591 A1  7/2008  Willson et al.

FOREIGN PATENT DOCUMENTS

| JP | 59-118090 | 7/1984 |
| JP | 61-254193 | 11/1986 |

(Continued)

OTHER PUBLICATIONS

Mata et al., Microalgae for biodiesel production and other applications: A review. Renewable and Sustainable Energy Reviews, vol. 14 (online Aug. 3, 2009) pp. 217-232.*

(Continued)

*Primary Examiner* — Jon P Weber
*Assistant Examiner* — Kara Johnson
(74) *Attorney, Agent, or Firm* — Antonelli, Terry, Stout & Kraus, LLP.

(57) ABSTRACT

The present invention provides a production method for biofuel based on a technology to convert carbon-dioxide as a carbon source through photosynthesis by photosynthetic microorganisms to biomass and produce biofuel of the biomass. The production method for biofuel of the present invention comprises a culturing process (S1) of culturing in a culture solution photosynthetic microorganisms which store oils, fats and carbohydrates in cells of the photosynthetic microorganisms, an oil and fat conversion process (S2) of converting the carbohydrates stored in the cells of the photosynthetic microorganisms cultured in the culture apparatus to oils and fats, an extraction process (S3) of extracting the oils and fats out of the cells of the photosynthetic microorganisms, and a reforming process (S4) to reform the extracted oils and fats.

20 Claims, 2 Drawing Sheets

(51) Int. Cl.
  C12P 7/64 (2006.01)
  C10L 1/02 (2006.01)

(56) References Cited

FOREIGN PATENT DOCUMENTS

| JP | 63-119409 | 5/1988 |
|----|-----------|--------|
| JP | 2010-57485 | 3/2010 |
| JP | 2010-514446 | 5/2010 |
| WO | WO 2009/076559 A1 | 6/2009 |

OTHER PUBLICATIONS

Coleman et al., Environmental control of carbohydrate and lipid synthesis in Euglena. Plant Cell Physiology, vol. 29 No. 3 (1988) pp. 423-432.*
Brennan et al. Biofuels from microalgae—A review of technologies for production, processing, and extractions of biofuels and co-products. Renewable and Sustainable Energy Reviews, vol. 14 (online Oct. 29, 2009) pp. 557-577.*
Yamane et al., Biomass production in mixotrophic culture of *Euglena gracilis* under acidic condition and its growth energetics. Biotechnology Letters, vol. 23 (2001) pp. 1223-1228.*
Singh et al., Lipid and hydrocarbon production by *Botryococcus* spp. under nitrogen limitation and anaerobiosis. World Journal of Microbiology and Biotechnology, vol. 8 (1992) pp. 121-124.*
Patent Examination Report No. 1, issued on May 28, 2013 in corresponding application No. 2011259331. Australian Patent Office.
Neeman, B.F., et al. Fuels from Microalgae: An Assessment of Technology Requirements, Energy from Biomass and Wastes X, 1987, pp. 1293-1308, vol. 10.
Suzuki, K., et al., "Introduction of Carbon Dioxide Fixation Technology by Microalgae—Our Company's Approaches to Business—", Biophilla, 2007, pp. 56-58, vol. 3, No. 2.
Suzuki, K., "Production of Useful Material from Microalgae *Euglena*", Abstracts of Annual Meeting in Chemical Society of Japan, Mar. 2011, p. 26,vol. 91, No. 1, No. 4 G4-14.
Notice of Rejection Reason dispatched on Aug. 5, 2014, in connection with Japanese Patent Application No. 2010-121042.
Extended European search report issued on Apr. 14, 2014, in connection with EP patent application No. 11786680.6.
The Office of Commercial Affairs, Royal Thai Embassy in Tokyo, Japan, Japan Economy's Digest, Mar. 2010, pp. 1-3.
Mata et al., "Microalgae for biodiesel production and other applications: A review", Renewable and Sustainable Energy Reviews, vol. 14, Jan. 2010.
Keck, "Innovative technology boosts algae potential", Ohio Farmer, Oct. 2009, p. 6.
Radakovits et al., "Genetic Engineering of Algae for Enhanced Biofuel Production", Eukaryoyic Cell, Apr. 2010, pp. 486-501.
Deng et al., "Microalgae: A promising feedstock for biodiesel", African Journal of Microbiology Research, vol. 3, Dec. 2009, pp. 1008-1014.
Teerawanichpan et al., "Fatty Acyl-CoA Redutase and Wax Synthase from *Euglena* gracilis in the Biosynthesis of Medium-Chain Was Esters", Lipids, 2010, pp. 263-273, vol. 45.
Tucci et al., "Variability of Wax Ester Fermentation in Natural and Bleached *Euglena* gracilis Strains in Response to Oxygen and the Elongase Inhibitor Flufenacet", The Journal of Eukaryotic Microbiology, Jan. 2010, pp. 63-69, vol. 57.
Sumi, "Microalgae Pioneearing the Future—Application and Utilization—", Quarter Review, Dec. 2009, pp. 9-21, vol. 34.
Third Party Submission filed Nov. 13, 2014 with JPO for Japanese Patent Application No. 2010-121042.
Translation of Excerpted Parts of Published Document Exhibit No. 1; (Japanese Patent Publication No. S59-118090) Cited in the Third Party Submission for Japanese Patent Application No. 2010-121042.

* cited by examiner

PRODUCTION METHOD FOR BIOFUEL

BACKGROUND OF THE INVENTION

Field of the Invention

The present invention relates to a production method for a biofuel to produce the biofuel.

The biofuel is a fuel produced from a raw material derived from biomass. If the biomass has a photosynthesis capability as ordinary plants have, it is possible to produce a fuel that has a smaller effect on the environment, because oils, fats and carbohydrates produced through the biomass from light energy, carbon-dioxide are raw materials for the biofuel. There are biofuels such as a bioethanol produced through alcohol fermentation of saccharified carbohydrate and a biodiesel oil and a biojetfuel which are produced from neutral lipids such as waxesters and triglycerides Although soy beans, corns and palms have been well known to be used for raw materials for the biofuel, there is an issue that using edible crops such as these crops leads to shortage of foods. Alternatively, non-edible crops such as jatropha and camelina are produced for the biofuel and there is a problem with these crops having a low yield for a unit area.

On the other hand, it is known that photosynthetic microorganisms and protozoa living in many lakes and marshes have the same photosynthesis capability as plants have and synthesize oils, fats and carbohydrates from water and carbon-dioxide and store in their cells an amount of oils, fats and carbohydrates, which corresponds to several tens percents of a dry weight of the photosynthetic microorganisms and protozoa. The photosynthetic microorganisms and protozoa are capable of producing a larger amount of oils, fats and carbohydrates than plants do and produce a more than ten times larger amount of oils, fats and carbohydrates for a unit area than palm which is said to be capable of producing a large amount of palm oils.

A patent document 1 describes fixing carbon-dioxide by culturing algae which are capable of photosynthesis by radiating the artificial light whose wave length and light intensity are artificially adjusted. The patent document 1 further describes a means, a method and a cultivation device to produce a target substance by fixing carbon-dioxide. Moreover the patent document 1 proposes fixing carbon-dioxide with photosynthetic microorganisms and making use of the fixed carbon-dioxide as a basic fuel for the biofuel as an example.

PRIOR ART DOCUMENT

Patent Document

Patent Document 1 JP2010-057485A

SUMMARY OF THE INVENTION

Objective to be Achieved by the Invention

However the patent document 1 does not disclose anything about how a biofuel is produced from the fixed carbon-dioxide. When the carbon-dioxide gas is reduced by making use of photosynthesis capability of microorganisms, the weight of the biomass increases in proportion to the amount of the fixed carbon-dioxide and it is difficult to make an industrial use of this invention if the biomass with the increased weight is effectively used.

The present invention is intended to provide a biofuel production method inclusive of a series of technologies to convert carbon-dioxide which is a carbon-source to the biomass through photosynthesis by photosynthetic microorganisms and subsequently produce a biofuel.

Means to Achieve the Objective

In order to achieve the objective above mentioned, the production method for biofuel of the present invention comprises a culturing process of culturing in a culture solution photosynthetic microorganisms which store oils, fats and carbohydrates in cells of the photosynthetic microorganisms, an oil and fat conversion process of converting the carbohydrates stored in the cells of the photosynthetic microorganisms cultured in the culture apparatus to oils and fats, an extraction process of extracting the oils and fats out of the cells of the photosynthetic microorganisms, and a reforming process to reform the extracted oils and fats.

According to the production method for biofuel of the present invention, the photosynthetic microorganisms are cultured in the culturing process, carbon-dioxide which is a carbon source is converted through photosynthesis by the photosynthetic microorganisms cultured in the culture solution to oils, fats and carbohydrates which are stored in cells of the photosynthetic microorganisms and the stored carbohydrates are converted to oils and fats. As a result, a larger amount of oils and fats than produced in any of the current production methods is efficiently produced. In addition, according to the production method for biofuel of the present invention, oils and fats are subsequently extracted in an extraction process and the extracted oils, fats are reformed in a reforming process that follows the extraction process and biofuel is produced.

Effect of the Invention

The present invention is intended to provide a biofuel production method inclusive of a series of technologies to convert carbon-dioxide which is a carbon source to the biomass through photosynthesis by photosynthetic microorganisms and subsequently produce a biofuel.

Moreover the present invention enables producing a larger amount of a biofuel than any of the current biofuel production methods, because it has a production process inclusive of an oil and fat conversion process.

DETAILED DESCRIPTION OF THE EMBODIMENTS

Hereinafter an embodiment of a biofuel production method of the present invention is explained with reference to FIG. 1.

Figure 1:
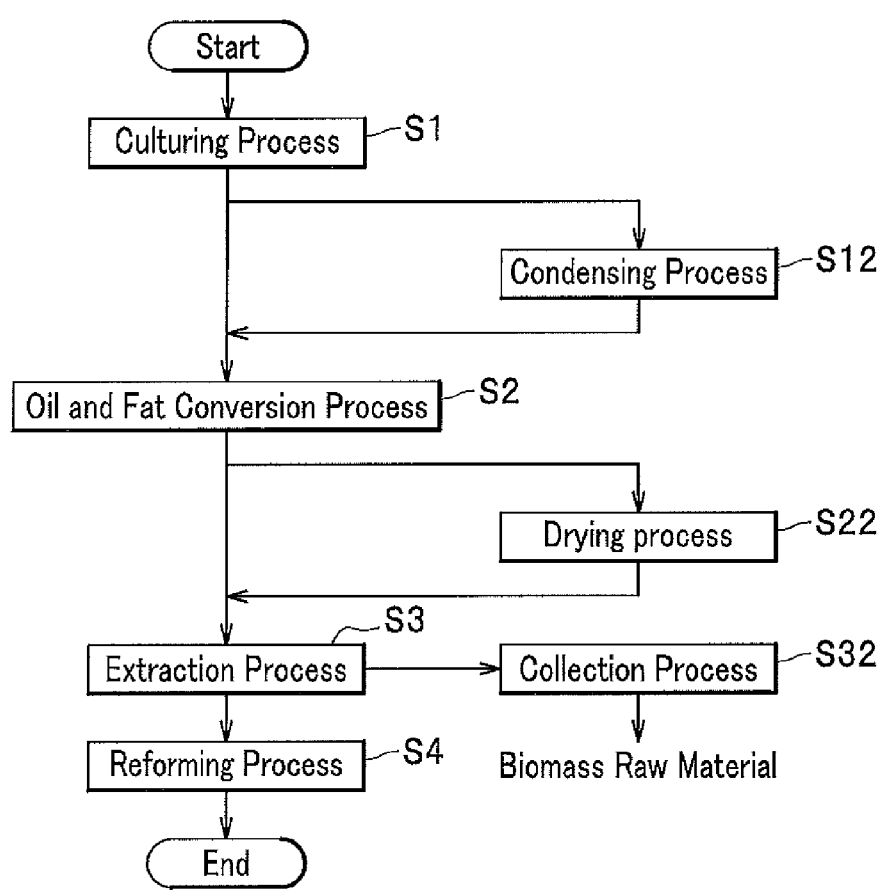
FIG. 1 is a flowchart explaining an embodiment for a biofuel production method of the present invention.

As shown in FIG. 1, the biofuel production method of the present invention includes a culturing process S1, an oil and fat conversion process S2, an extraction process S3 and a reforming process S4.

The culturing process S1 to be performed at first is a process to culture photosynthetic microorganisms which store oils, fats and carbohydrates in their cells in a culture solution.

*Euglena* is considered to be photosynthetic microorganisms to be used for the present invention. *Euglena* includes *Euglena gracilis* which belongs to a group of flagellates and is well known as a motile alga. Most of the *Euglena* have chlorophylls and live autotrophically through photosynthesis and there are some of the *Euglena* which are of a predator type or absorb nourishment from other organisms.

The *Euglena* is classified in both the zoology and the botany. In the zoology, a Euglenida, which is one of orders belonging to a Mastigophora and a Phytomastigophora in Protozoa, consists of three suborders, Eulenoidina, Peranemoidina and Petalomonadoidina. The Eulenoidina includes Genera, *Euglena*, *Trachelemonas*, *Strombonas*, *Phacus*, *Lepocinelis* and *Colacium*. In the botany, a Euglenales, which belongs to a Euglenophyceae in a Euglenophyta, includes genera such as the *Euglena*, as is the same way as in the zoology.

Besides the *Euglena* used for the present invention may be one or more of Cyanobacteria, Green algae and Trebouxiophyceae, Bangiophyceae, Prasinophyceae, Bacillasiophyceae, Coccolithophorid, Dinophyceae, Eustigmatophyceae and Chrysophyceae.

Examples of the Cyanobacteria for the present invention are Chroococcacae, Stigonematacae, Mastigocladacae and Oscillatroriacae and other examples are *Synechococcus* such as *Synechococcus lividus* and *Synechococcus elongatus*, *Synechocystis* such as *Synechocystis minervae*, *Mastigocladus* such as *Mastigocladus laminosus*, *Phormidium* such as *Phormidium laminosus*, *Symploca* such as *Symploca thermalis*, *Aphanocapsa* such as *Aphanocapsa thermalis* and *Fisherella*.

Furthermore *Anabanena variabilis* ATCC 29413 which belongs to genus *Anabaena*, *Cyanothece* sp. ATCC 51142 which belongs to genus *Cyanothece*, *Synechococcus* sp. PCC 7942 which belongs to genus *Synechococcus*, and *Anacystis nidulans* and *Thermosynechococcus elongatus* which belong to *Anacystis* may be used for the present invention.

Examples of green algae and Trebouxiophyceae for the present invention are *Cephaleuros* such as *Chlorella* inclusive of *Parachlorella* separated from *Chlorella* according to phylogenesis, *Chlamydomonas*, *Dunaliella*, *Scenedesmus*, *Botryococcus*, *Stichococcus*, *Nannochloris* and *Desmodesmus*. To be specific, examples of green algae and Trebouxiophyceae for the present invention are *Chlorella vulgaris* and *Chlorella saccharophila* included in *Chlorella*, *Dunaliella* such as *Dunaliella salina*, *Dunaliella tertiolecta* and *Parachlorella kessleri* (*Chlorella kessleri*) whose basic properties like photosynthesis are the same as *Chlorella* and *Dunaliella* and which are classified in Trebouxiophyceae according to the molecular phylogenic analysis, for example. In addition, there are such other examples for the present invention as *Chlamydomonas reinhardtii*, *Chlamydomonas moewusii*, *Chlamydomonas eugametos* and *Chlamydomonas segnis* which belong to *Chlamydomonas*, *Scenedesmus obliquus* which belongs to *Scenedesmus*, *Stichococcus ampliformis* which belongs to *Stichococcus*, *Nannochloris bacillaris* which belongs to *Nannochloris* and *Desmodesmus subspicatus* which belongs to *Desmodesmus*.

Furthermore, an example of Prasinophyceae for the present invention is *Tetraselmis* and examples of Bacillasiophyceae for the present invention are *Cyanidioschyzon*, *Cyanidium*, *Galdieria* and *Porphyridium*.

It should be noted that any microorganism may be used for the present invention as long as it is capable of producing oils, fats and carbohydrates, storing them in its cells and converting the stored carbohydrates to oils and fats and that the microorganisms to be used for the present invention should not be restricted to those above mentioned.

Though culturing photosynthetic microorganisms in the culturing process S1 may be carried out in the atmosphere, it is preferable to intentionally introduce the carbon-dioxide gas in the culture solution to increase the concentration of the carbon-dioxide dissolved in the culture solution to a higher one than the one for the condition in which the culture solution is just exposed to the atmosphere and increase the amount of oils, fats and carbohydrates that are produced through photosynthesis. For example, the carbon-dioxide gas discharged from factories and burning facilities may be used to intentionally introduce the carbon-dioxide gas in the culture solution. If the discharged carbon-dioxide gas is used, it is better to remove dust particles, NOx and SOx included in the exhaust gas through a dust collector, a denitration apparatus and a desulfuration apparatus in advance.

A liquid depth of the culture solution in the culturing process S1 is preferably equal to or less than 50 cm. More preferably the liquid depth of the culture solution in the culturing process S1 is equal to or less than 30 cm. If the liquid depth is kept as above mentioned, the culture solution is well stirred in the up-down direction (the upper liquid is frequently replaced with the lower liquid) when the photosynthetic microorganisms proliferate as the culturing progresses and the photosynthesis is being performed efficiently.

When *Euglena* are used as the photosynthetic microorganism, a culture medium to which a nitrogen source, a phosphorus source and minerals are added, such as a modified Cramer-Myers culture medium (including $(NH_4)_2HPO_4$ 1.0 g/L, $KH_2PO_4$ 1.0 g/L, $MgSO_4-7H_2O$ 0.2 g/L, $CaCl_2-2H_2O$ 0.02 g/L, $Fe_2(SO_2)_3-7H_2O$ 3 mg/L, $MnCl_2-4H_2O$ 1.8 mg/L, $CoSO_4-7H_2O$ 1.5 mg/L, $ZnSO_4-7H_2O$ 0.4 mg/L, $Na_2MoO_4-2H_2O$ 0.2 mg/L, $CuSO_4-5H_2O$ 0.02 g/L, thiamin chloride (vitamin $B_1$) 0.1 mg/L, and cyanocobalamin (vitamin $B_{12}$) and with pH3.5) may be used. Any of $(NH_4)_2HSO_4$ and $NH_3$aq may be used instead of $(NH_4)_2HPO_4$.

Any culture medium may be used for the present invention if it is fit for the photosynthetic microorganism to be used. The culture medium is not limited to the above mentioned one.

A pH of the culture solution is preferably between 2 and 6 and more preferably between 2 and 4.5. If the culture solution is acidic with its ph value kept as indicated above, the photosynthetic microorganism is capable of proliferating so well as to prevail over the other organisms, which enable suppressing contamination. As a result, a batch culture method as well as a continuous culture method may be used for the present invention.

The pH of the culture solution is appropriately adjusted with powder reagents and reagent solutions. One of the power reagents used for this pH adjustment may be sodium bicarbonate, and such acidic solutions as a sulfuric acid solution and an acetic acid solution and such a basic solution as a sodium hydroxide solution are examples of the reagent solutions.

The oil and fat conversion step S2 that follows the step S1 is a step to convert the carbohydrates stored in cells of the photosynthetic microorganisms which have been cultured in the culture solution to oils and fats.

The photosynthetic microorganisms stores oils and fats in their cells for self-defense when kept under anaerobic condition. Therefore, one of the methods for converting the carbohydrates stored in the photosynthetic microorganisms is, for example, to keep the culture solution in which the photosynthetic microorganisms have been cultured under anaerobic condition. In the present invention the anaerobic atmosphere refers to an atmosphere where there is no oxygen or less oxygen than in the atmosphere. The anaerobic condition is created according the following process. After the photosynthetic microorganisms are condensed in a condensation process S12 (sedimentation condensation and centrifugal separation), the photosynthetic microorganisms are kept in a closed space such as a closed container and a pipe, into which neither light nor oxygen comes, to prevent the photosynthetic microorganisms from producing oxygen through photosynthesis. Then oxygen in the closed space is consumed by the photosynthetic microorganisms respiration. As a result, the anaerobic condition is created. There may be other processes to create the anaerobic condition and the process to create the anaerobic condition is not limited to the above mentioned one. For example, the anaerobic condition is created by purging a space in which the photosynthetic microorganisms are kept with an inert gas like argon to remove oxygen.

In the present invention the condensation process S12 is preferably carried out before the oil and fat conversion process S2, that is, between the oil and fat conversion process S2 and the culturing process S1. During the condensation process S12, the photosynthetic microorganism, in whose cells oils, fats and carbohydrates are stored, are condensed and part of the culture solution that is not needed is removed. As a result, the subsequent process is easily carried out and this condensation process S12 enables creating the anaerobic atmosphere earlier because the oxygen dissolved in the condensed culture solution is completely consumed earlier through the photosynthesis by the photosynthetic microorganisms owing to the less culture solution left after the part of the culture solution is removed. Furthermore, the oil and fat conversion process progresses faster.

In the condensation process S12, the culture solution is condensed preferably through the sedimentation condensation followed by the centrifugal separation process.

Here the sedimentation condensation refers to having photosynthetic microorganism condensed through a natural sedimentation process such as leaving a solution inclusive of the photosynthetic microorganisms for 6 to 36 hours.

Condensation through the centrifugal separation process is to have photosynthetic microorganisms condensed by a centrifugal force on a centrifugal machine. Performing the centrifugal separation process on a solution inclusive of photosynthetic microorganisms, the solution is separated into a heavy solution with a higher specific gravity inclusive of the photosynthetic microorganisms and a light solution of a supernatant liquid with a lower specific gravity. Then by removing the light solution, the photosynthetic microorganisms contained in the heavy solution are appropriately condensed. Preferably as large an amount of the light solution as possible is removed. The centrifugal separation process may be performed with a centrifugal acceleration between 5.000 g and 20.000 g.

Both the supernatant liquid obtained after the sedimentation condensation and the light solution obtained after the centrifugal separation process may be put back into the culture solution to be used in the culturing step S1 and mixed with the culture solution. Thus the culture solution is more efficiently used. In addition the photosynthetic microorganisms which are contained in the supernatant liquid and the light solution and removed without being condensed are cultured again.

The photosynthetic microorganisms are kept at 25 to 40 degree centigrade with no light radiated on the photosynthetic microorganisms in the oil and fat conversion process S2. When the culture solution is kept under the conditioned above mentioned, carbohydrates stored in the cells are to be converted to oils and fats.

The extraction process S3 to be subsequently performed is to extract oils and fats from inside the cells of the photosynthetic microorganisms.

Oils and fats in the cells are to be extracted, for example, by a solvent extraction method with an organic solvent or a supercritical $CO_2$ extraction method. An organic solvent which may be used for the solvent extraction method is, for example, hexane. Since the hexane used for extracting oils and fats is reused for the solvent extraction after being distilled, this process has an advantage with respect to the environment and the production cost.

Such oils and fats as triglyceride and ester compounds (wax ester) made of a long chain fatty acid and a higher alcohol with one or two hydroxyl groups are extracted in this process.

It is preferable to perform a drying process S22 between the oil and fat conversion process S2 and the extraction process S3. In this drying process S22, the culture solution that contains the cultured photosynthetic microorganisms is dried. Since water which blocks the extraction is removed, oils and fats are more efficiently extracted after the drying process is performed.

Although the culture solution may be dried in the drying process through sun-dry, heated air dry or freeze drying method, it is preferable to make use of waste heat in exhaust gas or vapor discharged from factories or incineration plants. The culture solution is sufficiently dried without a need of other energies which work more rapidly and securely.

It is preferable to perform a collection process S32 after the extraction process S3. In the collection process S32 the photosynthetic microorganisms out of which oils and fats have been extracted in the extraction process S3 and which are defatted. The defatted photosynthetic microorganisms contain proteins that constitute cells and pigment components and are utilized for biomass raw materials such as feed, fertilizer, solid fuel and raw materials for chemical products.

A reforming process S4, in which the extracted oils and fats are modified, is subsequently performed.

Reforming oils and fats corresponds to a reduction process such as a hydrogenation reaction. For example, a biofuel such as gas oil and jet fuel is produced by removing oxygen in wax esters through the hydrogenation reaction.

Next, an embodiment of a biofuel production apparatus of the present invention is explained with reference to FIG. 2. The biofuel production apparatus shown in FIG. 2 corresponds to an example of a preferable embodiment of the production method for biofuel of the present invention.

Figure 2:
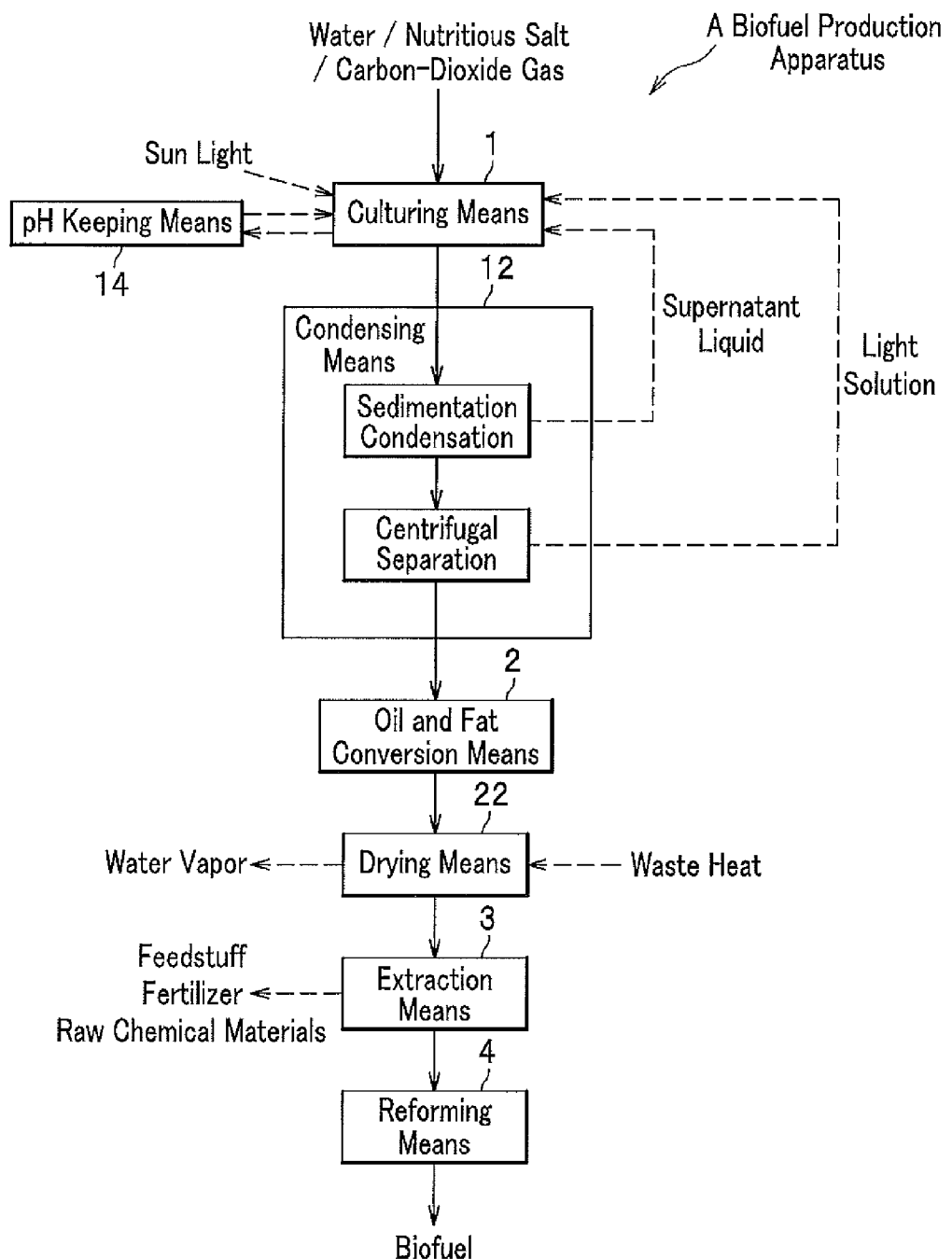
FIG. 2 is a block diagram explaining an embodiment for the biofuel production apparatus.

As shown in FIG. 2, a biofuel production apparatus A includes a culturing means 1, a condensing means 12 to condense the culture solution through sedimentation condensation and centrifugal condensation, an oil and fat converting means 2, a drying means 22 and an extraction means 4.

Each of these means corresponds to a process of the similar name. Therefore an explanation is skipped on significance, an act and an effect of each of these means which have been already explained in the description on the corresponding process.

The culturing means 1 may be, for example, a culture apparatus. The culture solution which is prepared for culturing photosynthetic microorganisms is put in the culture apparatus. In this embodiment, the culturing means 1 may be equipped with a carbon-dioxide gas supply means (not shown) to intentionally introduce into the culture apparatus carbon-dioxide gas which is a carbon source, a pH keeping means 14 to keep the pH of the culture solution between 2 and 6 in the acid region and a nutritious salt supply means (not shown) to supply nutritious salts to the culturing solution.

The culturing process may be performed with the culture apparatus exposed to the atmosphere without any cover to cover an upper side of the culture apparatus. If the cover is attached over the culture apparatus, it is preferable to have a light transmission means (not shown) through which sun light or illumination light transmits. The photosynthesis reaction progresses with the illumination light being radiated. Making use of the light transmission means and/or an illumination device, it is possible to have the photosynthesis of the photosynthetic microorganisms progress.

When a carbon-dioxide gas supply means is used, it is preferable to use an airtight culture apparatus in order not to have the carbon-dioxide gas leak. In addition, the culture apparatus may be equipped with a temperature sensor to measure a temperature of the culture solution or an inside of the culture apparatus, a light intensity sensor, a gas concentration sensor to measure a oxygen concentration or a carbon-dioxide concentration, a temperature control device to keep the temperature of the culture solution at a constant temperature and a stirring device to stir the culture solution (none of them shown).

A condensation means 12 to perform the sedimentation condensation is, for example, a sedimentation tank. When the sedimentation tank is disposed with an upper solution level in the sedimentation tank being higher than an upper solution level in the culture apparatus, the supernatant liquid in the sedimentation tank is transferred back into the culture apparatus due to a difference in the solution level between the sedimentation tank and the culture apparatus. The transferred supernatant liquid contains nutritious components and these nutritious components are reused and not wasted by transferring back the supernatant liquid.

A condensation means for the centrifugal separation process may be, for example, a centrifugal machine of a disk type. The light solution obtained after the centrifugal separation process may be put back into the culture apparatus to reduce an amount of water to be used. On the other hand, the heavy solution which has been condensed through the centrifugal separation process is supplied to the oil and fat conversion means 2.

An oil and fat conversion means 2 may be, for example, an airtight tank which is capable of blocking light coming therein. This airtight tank may be equipped with a temperature control device to keep the temperature of the condensed culture solution at a constant temperature, and a gas concentration sensor to measure a oxygen concentration or a carbon-dioxide concentration, and may be further equipped with a gas introduction means and a gas discharge means which are constituted by one way valves and other components if oxygen is purged from the airtight tank by having an inert gas such as nitrogen or argon flow in the airtight tank to keep the airtight tank under the anaerobic condition.

A drying means 22 may be, for example, a drying machine making use of waste heat in waste gas or waste vapor discharged from factories or incineration plants. The drying machine for the present invention is not limited to this type and may be a heated air drying machine that is commercially available or a freeze dry drying machine. In addition, the drying process S22 may be performed through sun-dry as has been explained. Water included in the culture solution is evaporated to water vapor and removed.

The extraction means 3 may be, for example, a solvent extraction apparatus to extract oils and fats with an organic solvent or a supercritical $CO_2$ extraction which extracts oils and fats with $CO_2$ in a supercritical condition. Organic solvents such as hexane may be used for this extraction process, as has been mentioned.

As has been explained for the extraction process 3, the defatted microorganisms from which oils and fats have been extracted are collected and used for such raw biomass materials as feedstuff, fertilizer, solid fuel, and raw materials for chemical products after organic components of the defatted microorganism are biologically or chemically dissolved or dried.

A reforming means may be, for example, such a hydrodesulfurization unit as a hydrodesulfurization unit for kerosene and gas oil, a hydrodesulfurization unit for vacuum gas oil, a naphtha hydrorefining unit and a hydrodesulfurization unit for heavy oil, which perform hydrogenation reactions. Among these units, the hydrodesulfurization unit for kerosene and gas oil is capable of efficiently producing such a biofuel as gas oil and jet fuel.

EXAMPLE

Hereinafter is explained a production method for biofuel of the present invention specifically, with reference to an example.

This example utilizes *Euglena* as photosynthetic microorganisms.

Firstly, a modified Cramer-Myers culture medium (including $(NH_4)_2HPO_4$ 1.0 g/L, $KH_2PO_4$ 1.0 g/L, $MgSO_4-7H_2O$ 0.2 g/L, $CaCl_2-2H_2O$ 0.02 g/L, $Fe_2(SO_2)_3-7H_2O$ 3 mg/L, $MnCl_2-4H_2O$ 1.8 mg/L, $CoSO_4-7H_2O$ 1.5 mg/L, $ZnSO_4-7H_2O$ 0.4 mg/L, $Na_2MoO_4-2H_2O$ 0.2 mg/L, $CuSO_4-5H_2O$ 0.02 g/L, thiamin chloride (vitamin $B_1$) 0.1 mg/L, and cyanocobalamin (vitamin$B_{12}$) and with pH3.5) was prepared by adding nutritious salts such as a nitrogen source, a phosphor source and minerals into water stored in a culture apparatus.

*Euglena* was inoculated in the prepared culture solution and cultured for seven days with sun light radiated on the *Euglena*. A temperature of the culture solution was kept within a range of 29° C.±3° C. during the culture period. Carbon-dioxide gas was introduced in the culture apparatus during the culture period. The pH of the culture solution became lower for an acid with the carbon-dioxide gas being introduced and was kept in a acidic range between 2 and 6 with a pH keeping apparatus. When *Euglena* was cultured in the culture media whose pH is approximately between 2 and 4.5, it was difficult for other microorganisms to breed and contamination was effectively prevented.

The liquid depth of the culture solution was kept less than or equal to 50 cm. However when the liquid depth of the culture solution was kept less than or equal to 30 cm, photosynthetic reaction progressed more efficiently because the culture solution in the lower portion was efficiently replaced with the culture solution in the upper portion by stirring the culture solution. A predetermined amount of the culture solution in the culture apparatus was taken out of the culture apparatus and transferred into a sedimentation tank. Since the *Euglena* had a larger specific gravity than that of water, the *Euglena* settled on the bottom of the sedimentation tank through a natural sedimentation process in which the *Euglena* was coming down toward the bottom of the sedimentation tank. A predetermined amount of the culture solution inclusive of the settled *Euglena* was transferred into a centrifugal machine. The supernatant liquid was transferred back into the culture apparatus after centrifugal separation process and used again for culturing *Euglena*.

In the centrifugal separation process, the condensed solution which included the *Euglena* and transferred into a centrifugal machine was centrifuged. Then a heavy solution which included the *Euglena* further condensed and had a higher concentration the *Euglena* was obtained. Subsequently this condensed heavy solution was sent to the oil and fat conversion process. A light solution including the *Euglena* which was not separated into the heavy solution was transferred into the culture apparatus and used again for culturing *Euglena*.

In the oil and fat conversion process, the heavy solution was kept in the anaerobic atmosphere to accelerate metabolism in the cultured *Euglena* and increase their content rate of oils and fats. In this process, the heavy solution was kept between 25° C. and 40° C. under the anaerobic condition with no sun light being radiated on the heavy solution. When the oil and fat conversion process was performed on the culture solution which was not condensed in the condensing process, an amount of the culture solution, in which oxygen discharged by the *Euglena* through the photosynthetic reaction was dissolved, is so large that it took a longer time to decrease the concentration of oxygen dissolved in the culture solution and suppress respiration of the cultured *Euglena*. Therefore a larger amount of an inert gas had to be used to create the anaerobic condition. On the other hand, when the oil and fat conversion process was performed on the cultured solution that was condensed in the condensing process, the amount of the culture solution, in which a concentration of the *Euglena* was higher and oxygen discharged by the *Euglena* through photosynthetic reaction was dissolved, was not so large and it did take a shorter time to decrease the concentration of oxygen dissolved in the culture solution. As a result, the amount of the inert gas to create the anaerobic condition became smaller.

Next, the *Euglena*, whose content rate of oils and fats was increased by the anaerobic process, was dried at 110° C. on the waste heat for 120 minutes.

Oils and fats were extracted out of the dried stuff in the dried *Euglena* through a solvent extraction method with hexane and the dried *Euglena* was divided in oils and fats and the defatted dried stuff of the *Euglena*.

By purifying oils and fats through a hydrodesulfurization unit for kerosene and gas oil, petroleum substitute fuel (biofuel) was produced. This petroleum substitute fuel is presumed to be capable of being used for gas oil and jet fuel because it consists mainly of oils and fats of carbon compounds whose carbon length is fourteen.

In addition, the defatted *Euglena* was collected and utilized for raw biomass materials to be used for feedstuff and fertilizer.

Description of Signs
S1 Culturing process
S12 Condensing process
S2 Oil and fat conversion process
S22 Drying process
S3 Extraction process
S32 Collection process
S4 Reforming process
A Biofuel production apparatus
1 Culturing means
12 Condensing means
14 pH keeping means
2 Oil and fat converting means
22 Drying means
3 Extracting means
4 Reforming means

What is claimed is:

1. A production method for biofuel comprising;
a culturing process of culturing in a culture solution photosynthetic microorganisms which store oils, fats and carbohydrates in cells of the photosynthetic microorganisms;
a condensing process of condensing the culture solution in which the photosynthetic microorganisms are cultured, the condensing process being performed after the culturing process, the condensing process comprising removing a light solution supernatant liquid from the culture solution to produce a condensed culture solution;
an oil and fat conversion process of converting the carbohydrates stored in the cells of the photosynthetic microorganisms cultured in the condensed culture solution to oils and fats under an anaerobic condition, after the condensing process;
an extraction process of extracting the oils and fats out of the cells of the photosynthetic microorganisms, and
a reforming process to reform the extracted oils and fats, wherein the photosynthetic microorganisms are *Euglena*.

2. The production method for biofuel as described in claim 1 further wherein condensing the culture solution is performed through sedimentation condensation in the condensing process.

3. The production method for biofuel as described in claim 2 further wherein the culture solution is condensed through centrifugal separation following the sedimentation condensation.

4. The production method for biofuel as described in claim 3 wherein putting the supernatant liquid obtained through the centrifugal separation back into the culture apparatus used in the culturing process.

5. The production method for biofuel as described in claim 2 wherein putting the supernatant liquid obtained through the sedimentation condensation back into the culture apparatus used in the culturing process.

6. The production method for biofuel as described in claim 1 further comprising a drying process of drying the culture solution inclusive of the cultured photosynthetic microorganisms between the oil and fat conversion process and the extraction process.

7. The production method for biofuel as described in claim 1 further comprising a collection process of collecting the defatted photosynthetic microorganisms out of which oils and fats are extracted after the extraction process.

8. The production method for biofuel as described in claim 1 wherein culturing the photosynthetic microorganisms is performed in the culture solution with a concentration of dissolved carbon-dioxide concentration that is higher than one which ambient air is introduced.

9. The production method for biofuel as described in claim 1 wherein a liquid depth of the culture solution in the culturing process is less than or equal to 50 cm.

10. The production method for biofuel as described in claim 1 wherein a pH of the culture solution in the culturing process is kept between 2 and 6.

11. The production method for biofuel as described in claim 1 wherein in the oil and fat conversion process the culture solution is kept between 25° C. and 40° C. and no light is radiated on the culture solution.

12. A production method for biofuel comprising;
a culturing process of culturing in a nitrogen containing culture solution photosynthetic microorganisms which store oils, fats and carbohydrates in cells of the photosynthetic microorganisms;
a condensing process of condensing the nitrogen containing culture solution in which the photosynthetic microorganisms are cultured, the condensing process being performed after the culturing process, the condensing process comprising removing a light solution supernatant liquid from the culture solution to produce a condensed culture solution;

an oil and fat conversion process of converting the carbohydrates stored in the cells of the photosynthetic microorganisms to oils and fats comprising culturing the photosynthetic microorganisms under an anaerobic condition in the condensed nitrogen containing culture solution after the condensing process;

an extraction process of extracting the oils and fats out of the cells of the photosynthetic microorganisms, and a reforming process to reform the extracted oils and fats, wherein the photosynthetic microorganisms are *Euglena*.

13. The production method for biofuel as described in claim 12 further wherein condensing the culture solution is performed through sedimentation condensation in the condensing process.

14. The production method for biofuel as described in claim 13 further wherein the culture solution is condensed through centrifugal separation following the sedimentation condensation.

15. The production method for biofuel as described in claim 12 further comprising a drying process of drying the culture solution inclusive of the cultured photosynthetic microorganisms between the oil and fat conversion process and the extraction process.

16. The production method for biofuel as described in claim 12 further comprising a collection process of collecting the defatted photosynthetic microorganisms out of which oils and fats are extracted after the extraction process.

17. The production method for biofuel as described in claim 12 wherein culturing the photosynthetic microorganisms is performed in the condensed nitrogen containing culture solution with a concentration of dissolved carbon-dioxide concentration that is higher than one which ambient air is introduced.

18. The production method for biofuel as described in claim 12 wherein a liquid depth of the nitrogen containing culture solution in the culturing process is less than or equal to 50 cm.

19. The production method for biofuel as described in claim 12 wherein a pH of the culture solution in the culturing process is kept between 2 and 6.

20. The production method for biofuel as described in claim 12 wherein in the oil and fat conversion process the condensed nitrogen containing culture solution is kept between 25° C. and 40° C. and no light is radiated on the condensed nitrogen containing culture solution.

* * * * *